(12) United States Patent
Weissman et al.

(10) Patent No.: US 6,308,715 B1
(45) Date of Patent: Oct. 30, 2001

(54) ULTRASONIC DETECTION OF RESTENOSIS IN STENTS

(75) Inventors: Eric M. Weissman, Chagrin Falls; Elmer D. Dickens, Jr., Richfield, both of OH (US); William B. Spillman, Jr., Floyd, VA (US)

(73) Assignee: PMD Holdings Corp., Brecksville, OH (US)

( * ) Notice: Subject to any disclaimer, the term of this patent is extended or adjusted under 35 U.S.C. 154(b) by 0 days.

(21) Appl. No.: 09/512,183

(22) Filed: Feb. 24, 2000

Related U.S. Application Data

(63) Continuation-in-part of application No. 09/275,311, filed on Mar. 24, 1999, now Pat. No. 6,170,488.

(51) Int. Cl.⁷ .................................................. A61B 19/00
(52) U.S. Cl. ............................................ 128/899; 600/437
(58) Field of Search .................................. 600/456, 454, 600/459, 500, 504, 505, 437; 601/2; 73/579, 584; 128/897, 899, 903; 623/1.1, 1.3, 11, 12; 607/60, 61, 65

(56) References Cited

U.S. PATENT DOCUMENTS

| | | | |
|---|---|---|---|
| 3,477,422 | * 11/1969 | Jurist, Jr. et al. | 600/552 |
| 3,640,271 | * 2/1972 | Horton | 600/438 |
| 3,853,117 | * 12/1974 | Murr | 600/438 |
| 4,107,775 | * 8/1978 | Ott | 364/413 |
| 4,114,606 | 9/1978 | Seylar | 600/409 |
| 4,352,960 | 10/1982 | Dormer et al. | 607/57 |
| 5,392,779 | * 2/1995 | Meredith et al. | 600/437 |
| 5,749,909 | 5/1998 | Schroeppel et al. | 607/33 |
| 5,891,180 | 4/1999 | Greeninger et al. | 607/32 |
| 5,967,986 | 10/1999 | Cimochowski et al. | 600/454 |
| 5,967,989 | 10/1999 | Cimochowski et al. | 600/459 |
| 5,972,029 | 10/1999 | Fuisz | 623/1 |
| 5,989,190 | * 11/1999 | Kaplan | 600/438 |
| 6,015,386 | 1/2000 | Kensey et al. | 600/486 |
| 6,053,873 | * 4/2000 | Govari et al. | 600/505 |
| 6,083,165 | * 7/2000 | Kaplan | 600/438 |

* cited by examiner

Primary Examiner—John P. Lacyk
Assistant Examiner—Charles Marmor, II
(74) Attorney, Agent, or Firm—Thoburn T. Dunlap; Brian M. Kolkowski; Mark D. Saralino

(57) ABSTRACT

An analyzer apparatus and method is provided for analyzing restenosis associated with a stent implanted within a living body. The apparatus includes an input for receiving ultrasonic data from an ultrasonic imaging apparatus; digital memory for storing the ultrasonic data at least temporarily; a processor for analyzing the ultrasonic data, the processor being configured to analyze the data in accordance with at least one predefined criteria to diagnose a degree of restenosis experienced by the stent; and an output for outputting information indicative of the diagnosis.

25 Claims, 16 Drawing Sheets

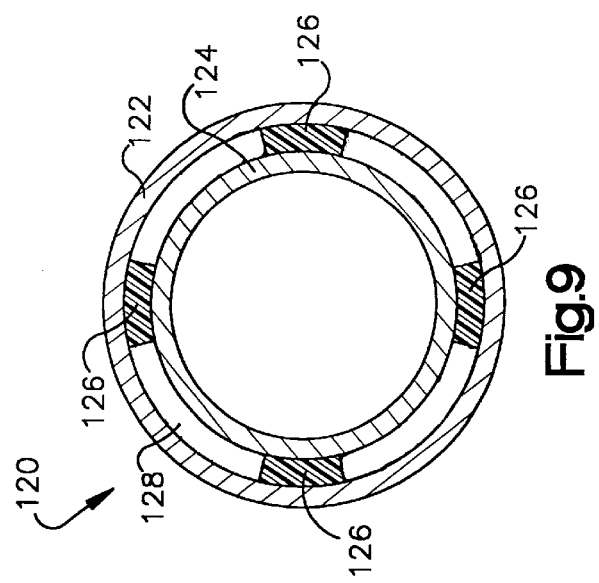
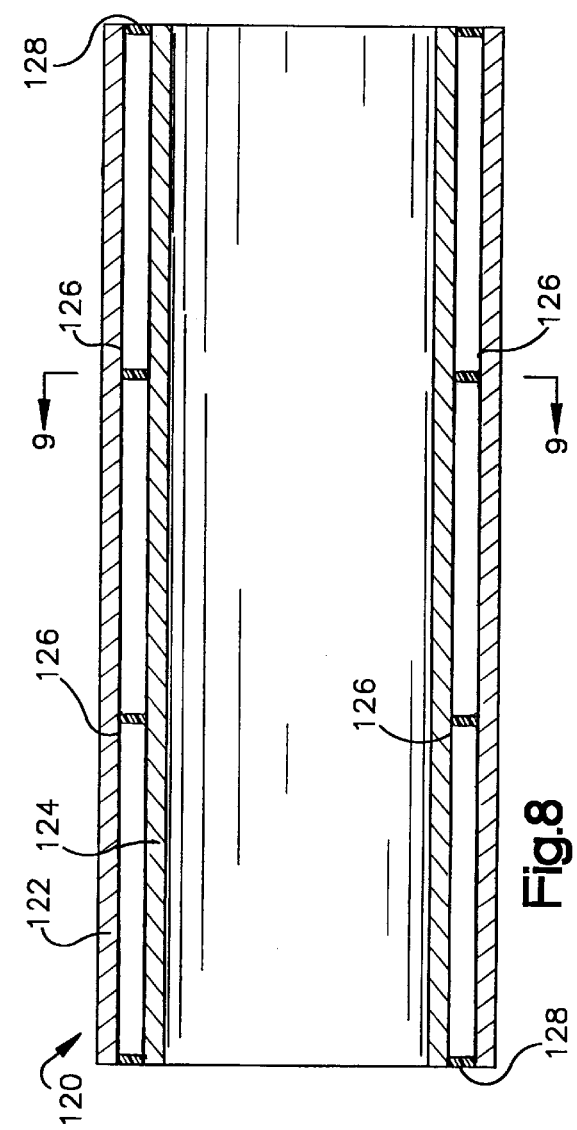

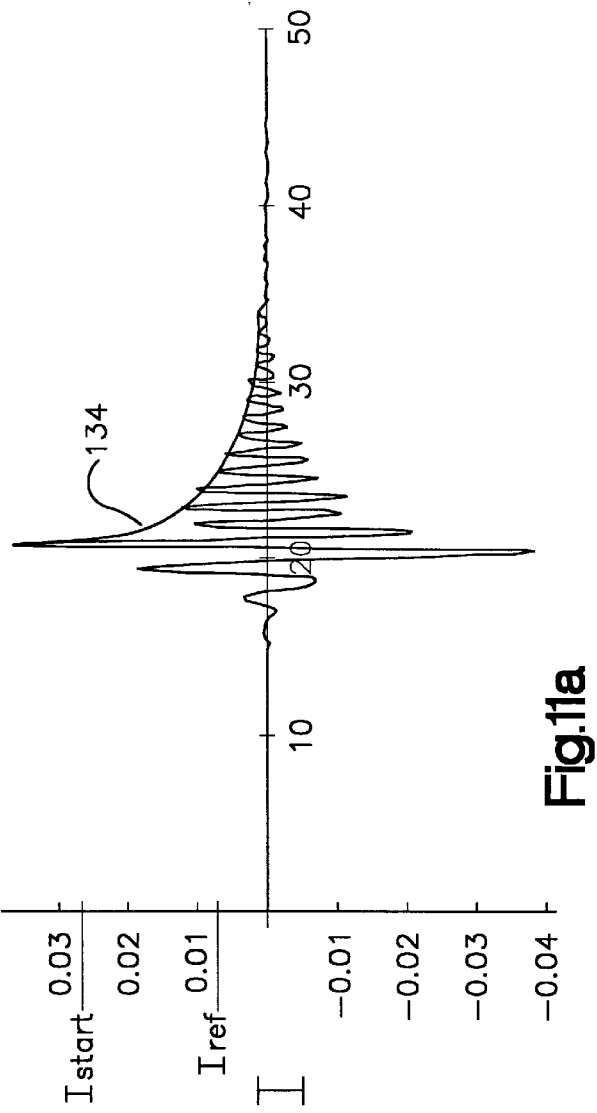
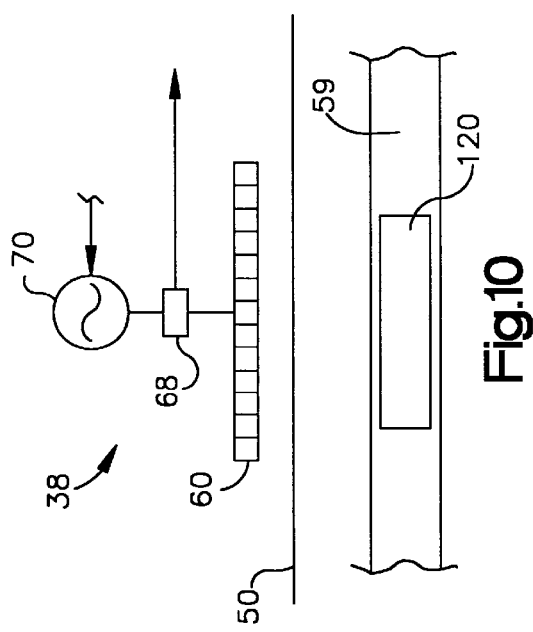
Fig.11a
Fig.10

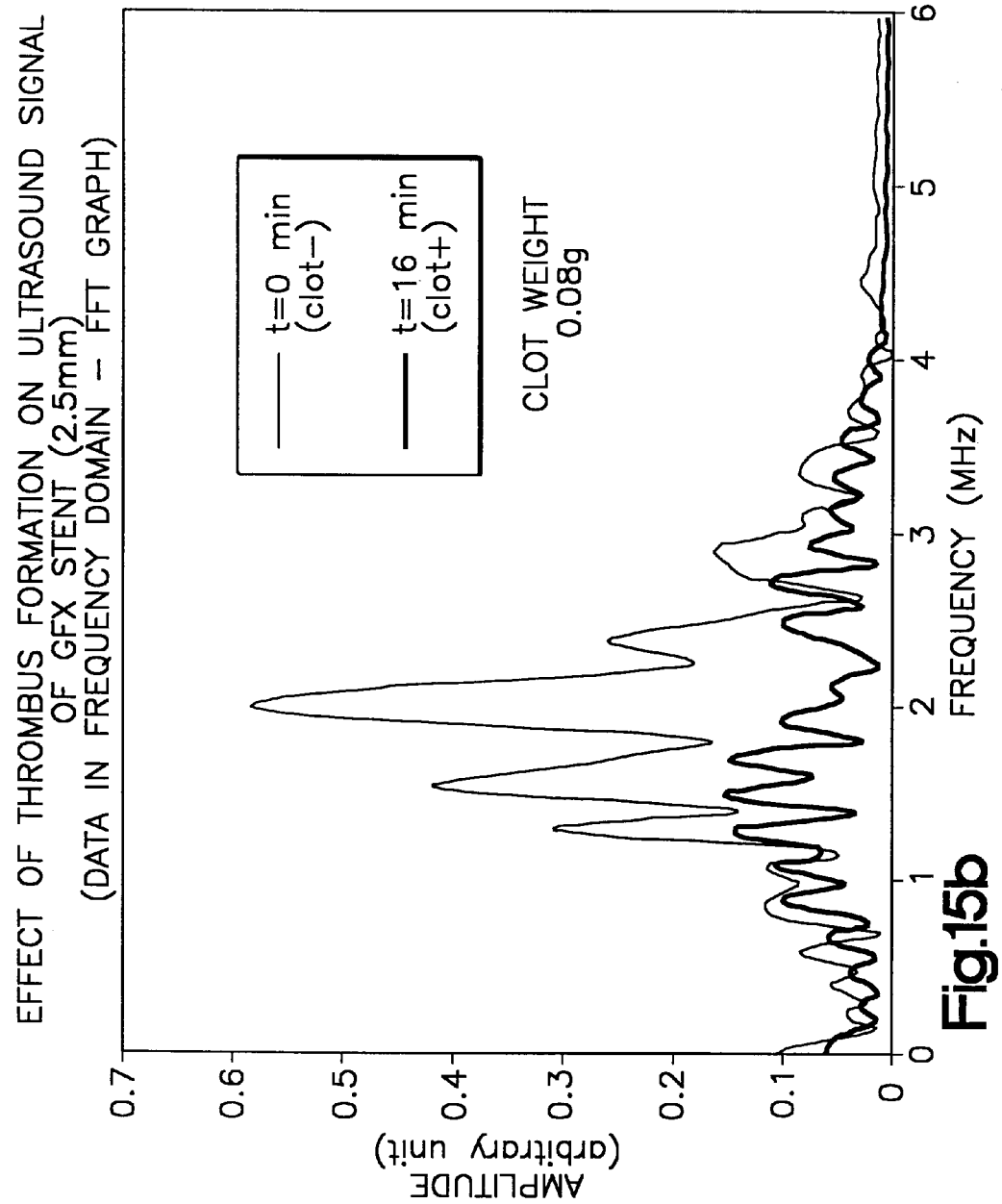

ULTRASONIC DETECTION OF RESTENOSIS IN STENTS

CROSS-REFERENCE TO RELATED APPLICATION

This is a continuation-in-part of commonly owned, application Ser. No. 09/275,311, filed on Mar. 24, 1999, now U.S. Pat. No. 6,170,488 the entire disclosure of which is incorporated herein by reference.

TECHNICAL FIELD

The present invention relates generally to non-invasive diagnoses of medical implant devices, and more particularly to ultrasonic detection of restenosis in a stent.

BACKGROUND OF THE INVENTION

Various types of medical implant devices have been developed over the years. In many instances, such devices enable humans to live longer, more comfortable lives. Implant devices such as pacemakers, artificial joints, valves, grafts, stents, etc. provide a patient with the opportunity to lead a normal life even in the face of major heart, reconstructive, or other type surgery, for example.

It has been found, however, that the introduction of such implant devices can sometimes lead to complications. For example, the human body may reject the implant device which can ultimately lead to infection or other types of complications. Alternatively, the implant device may malfunction or become inoperative. Therefore, it is desirable to be able to monitor the condition of the implant device. On the other hand, it is highly undesirable to have to perform invasive surgery in order to evaluate the condition of the device.

Still further, it is desirable to be able to monitor conditions related to the use of implant devices. For example, in heart patients it may be helpful to know the amount of blood flowing through a stent in order to evaluate the health of the patient. Again, however, it is undesirable to have to perform invasive surgery in order to evaluate such conditions.

Techniques have been developed which enable the function of an implant device to be monitored remotely from outside the body of the patient. These techniques involve including one or more sensors in the device for sensing the condition of the device. The device further includes a small transceiver for processing the output of the sensors and transmitting a signal based on the output. Such signal typically is a radio frequency signal which is received by a receiver from outside the body of the patient. The receiver then processes the signal in order to monitor the function of the device.

While such conventional techniques may be effective in avoiding the need to perform invasive surgery, there are however several drawbacks associated therewith. For example, the transceiver included in the implant device typically includes complex electrical circuitry such as mixers, amplifiers, microprocessors, etc. for receiving an interrogation signal and for transmitting a response signal based on the output of the sensors. Such complex circuitry has a relatively high cost associated therewith. In addition, the complexity of the circuitry increases the likelihood that the device itself may be defective. This would then require further invasive surgery and could even result in physical harm to the patient.

Still another shortcoming with conventional implant devices with sensors included therein is power concerns. Some type of circuit for providing power to the transceiver is necessary. The circuit may be a built-in power source such as a battery, or a circuit which derives operating power from an external excitation signal using magnetic or electromagnetic coupling. In either case, again the complexity of the circuit and/or the need to replace the battery periodically adds to the cost of the device and increases the opportunity for failure or defects.

In view of the aforementioned shortcomings associated with conventional implant devices, there is a strong need in the art for a medical implant system and method, particularly with respect to a stent, which can remotely interrogate the stent but which does not require complex electrical circuitry such as mixers, amplifiers, microprocessors, etc. There is a strong need for a stent which carries out its function within a human or other living animal, and can be remotely interrogated simply and reliably. Moreover, there is a strong need for a stent which does not rely on complex energy conversion circuits in order to operate.

SUMMARY OF THE INVENTION

According to one aspect of the invention, a diagnostic system is provided. The system includes a stent implantable within a blood vessel of a living animal and operatively configured to prevent the vessel from collapsing. The stent may be a typical commercially available stent or one specially designed to exhibit a mechanical transfer function which, in response to mechanical excitation, causes the structure to produce an acoustic signal having a characteristic which is modulated in relation to the presence of restenosis within the stent. The system further includes an exciter for acoustically transferring mechanical energy to the stent from outside the living animal, and a receiver located outside the living animal which detects the acoustic signal produced by the structure, processes the acoustic signal in relation to the mechanical transfer function, and provides an output indicative of the parameter based on the processed acoustic signal.

The system may be based on existing ultrasonic imaging equipment, or can comprise a system designed specifically for analyzing a stent. A combination of software and/or hardware is provided for analyzing ultrasonic data reflected or reradiated from the stent in response to ultrasonic pulses. The data is digitized and processed using one or more algorithms such as a Fast Fourier Transform (FFT), wavelets, etc. By analyzing response parameters such as amplitude, harmonic content, phase and/or modulus data as a function of frequency, for example, it has been found that the degree of restenosis within the stent may be diagnosed. A signature database for storing response data for one or more standard stents of different sizes, types, manufacturers, etc., is provided. The system uses a pattern recognition or matching algorithm to identify the particular stent within the body, and uses such information to normalize the acquired data, set baselines, etc.

A feature of the invention is that it can be implemented with limited hardware and/or software in combination with conventional ultrasonic imaging equipment. Alternatively, the present invention may be carried out as an entirely new system configured specifically for the detection of restenosis in stents.

To the accomplishment of the foregoing and related ends, the invention, then, comprises the features hereinafter fully described and particularly pointed out in the claims. The following description and the annexed drawings set forth in detail certain illustrative embodiments of the invention.

These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 8 is a cross-section view of a dual-cylinder stent in accordance with the present invention;

FIG. 9 is a cross-section view taken along line 9—9 of the stent in FIG. 8 in accordance with the present invention;

FIG. 10 is schematic view representing an acoustic source/detector and the stent of FIGS. 8 and 9 in accordance with the present invention;

FIGS. 11a and 11b are graphs illustrating a change in resonance decay time as a function of degree of restenosis in accordance with the present invention;

FIGS. 15a, 15b and 15c illustrate attenuation exhibited by commercially available stents as a function of the amount of restenosis built up therein;

DESCRIPTION OF THE PREFERRED EMBODIMENTS

Figure 1:
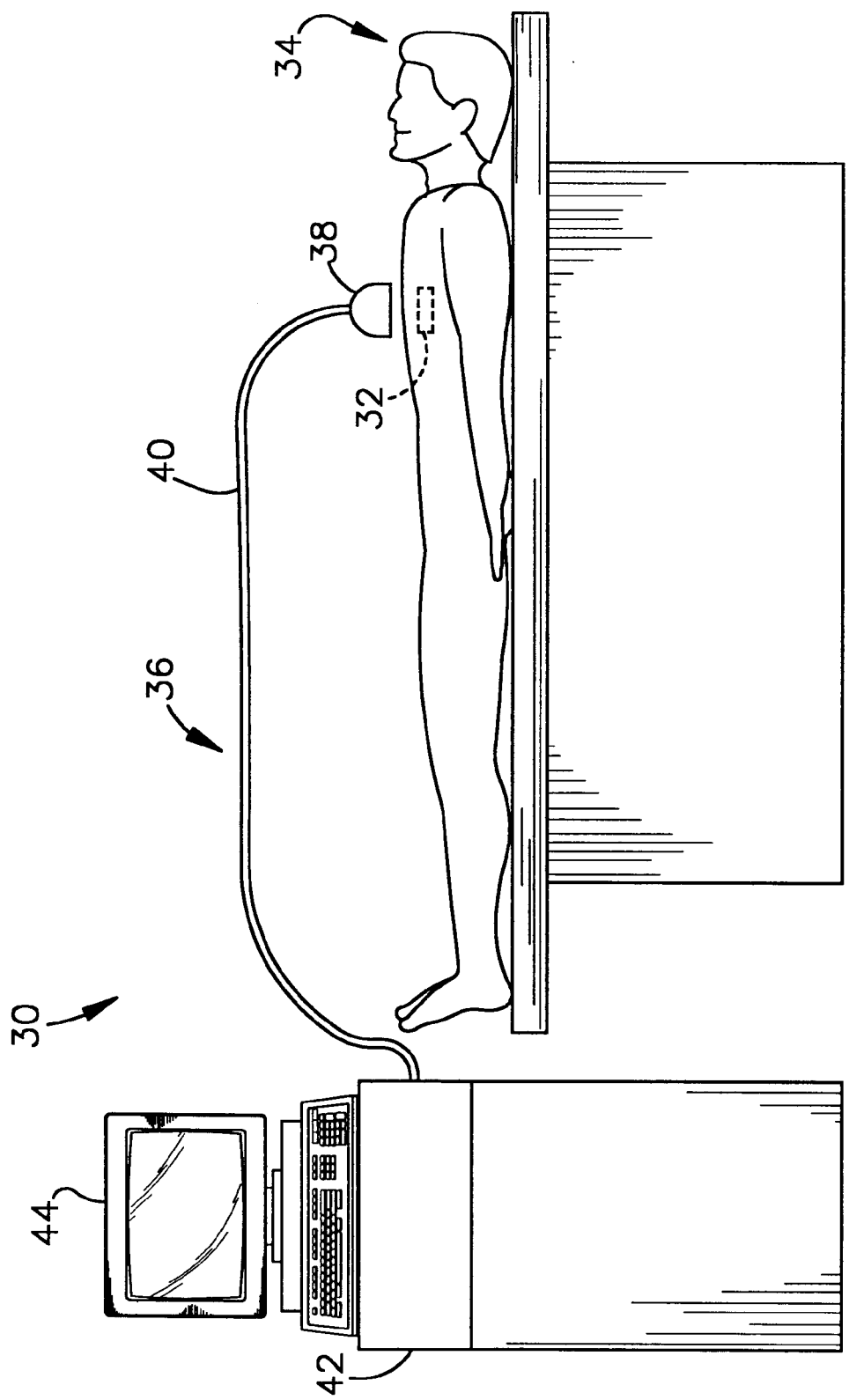
FIG. 1 is an environmental view illustrating a system including a remotely interrogated medical implant device, such as a stent, and broadband acoustic analyzer in accordance with the present invention.

The present invention will now be described with reference to the drawings, wherein like reference numerals are used to refer to like elements throughout.

Referring initially to FIG. 1, a system for remotely interrogating a medical implant device according to the invention is generally designated 30. The system 30 includes a medical implant device 32 which is implanted in a living animal such as a human patient 34. As is discussed in more detail below, the medical implant device 32 can be any of a wide variety of different types of devices including, for example, a stent, graft, artificial joint, etc. In the preferred embodiment, the device is a stent.

The device 32 preferably is configured to carry out or assist in carrying out a function within the patient 34. For example, in the case of a stent the device 32 prevents the closing of an arterial wall and permits the flow of blood therethrough. In the case of a graft, the device 32 serves to couple blood flow between two separate ends of a blood vessel. The device 32 may instead consist of an artificial hip or knee which facilitates movement of the leg of the patient 34. Other type devices include, but are not limited to, a hemodialysis shunt and spinal brace, for example.

The system 30 further includes an acoustic analyzer 36 for remotely powering and/or interrogating the implant device 32 in order to evaluate the device function. The analyzer 36 in the exemplary embodiment includes a broadband acoustic source/detector unit 38 which is positioned outside the patient 34 in close proximity to the implant device 32. As will be discussed in more detail below, the source/detector unit 38 serves to excite the device 32 with acoustic energy. The acoustic energy is used to evaluate the mechanical transfer function of the device 32. The source/detector unit 38 may then receive acoustic signals reradiated and/or reflected by the device 32 in response to the excitation. Such signals can then be processed by the analyzer 36 to detect a parameter of interest (e.g., amount of restenosis, etc.).

The source/detector unit 38 is coupled via an electrical cable 40 to the main circuitry 42 included in the analyzer 36. The main circuitry 42 includes suitable circuits for driving the source/detector unit 38 as described below, and for processing the output of the source/detector unit 38 in order to provide an output to an operator (e.g., display 44).

As will be better understood based on the description which follows, the present invention utilizes acoustic coupling between the source/detector unit 38 and the implant device 32. The device 32 is designed to respond to acoustic energy transmitted by the source/detector 38 in a manner which eliminates the need for complex electronics, power supplies, etc. within the device. In this manner, the device 32 can be a very simple, relatively low cost device which is less prone to failure. The device 32 does not require an active transmitter, mixer, amplifier, etc. as in other conventional devices. Moreover, the patient 34 is exposed to less high frequency radiation as compared to other types of remotely interrogated implant devices, thus improving the safety of the device.

Figure 2:
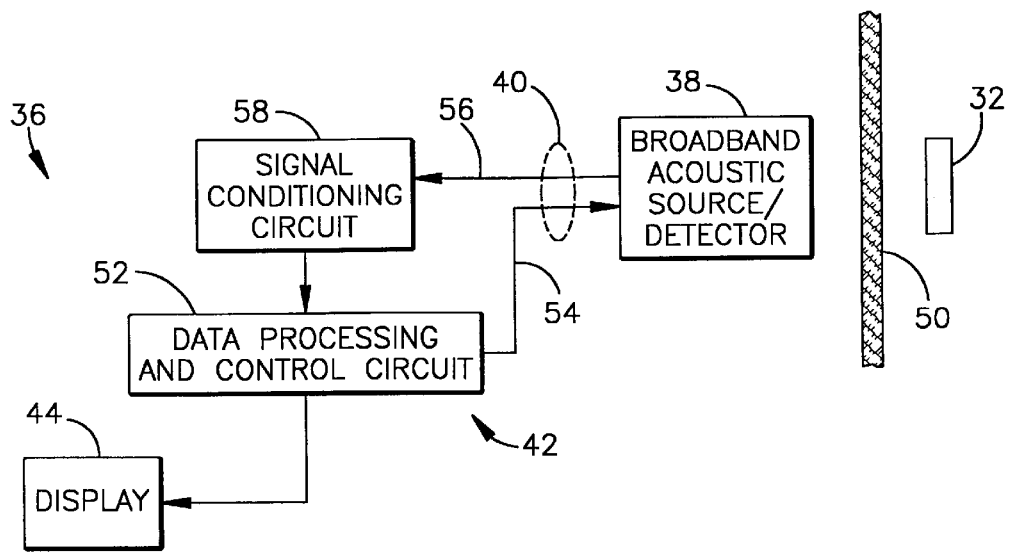
FIG. 2 is a block diagram of the broadband acoustic analyzer in accordance with the present invention.

Referring now to FIG. 2, the acoustic analyzer 36 in accordance with the exemplary embodiment is illustrated in more detail. The source/detector unit 38 preferably is a hand-held sized device which is held by a doctor, nurse or medical assistant outside the body of the patient 34 in close proximity to the implant device 32. Since the system 30 is non-invasive, the source/detector unit 38 may be placed adjacent the implant device 32 with the body of the patient (e.g., skin, muscle tissue, etc.), designated 50, disposed therebetween.

The analyzer 36 includes a data processing and control circuit 52 which is programmed to carry out the various control and computational functions described herein. More particularly, the circuit 52 provides a control signal on control bus 54. The control signal controls the frequency (within the acoustic frequency band) at which the source/detector 38 excites the device 32 by emitting acoustical energy while positioned in close proximity to the device 32 as shown. In addition, the control circuit 52 provides a control signal on bus 54 in order to control whether the source/detector 38 is transmitting acoustic energy or receiving acoustic energy reradiated/reflected from the device 32 in response to being excited.

The source/detector 38 receives acoustic energy from the device 32 based on the mechanical transfer function of the device 32, and converts the energy into an electrical signal on line 56. The signal on line 56 is input to a signal conditioning circuit 58 which conditions the signal prior to being input to the data processing and control circuit 52. As is discussed more fully below, the data processing and control circuit 52 processes and analyzes the signal on line 56 in order to determine a parameter associated with the device. For example, the excitation signal from the source/detector 38 is used to induce a mechanical resonance in the device 32. The source/detector 38 then detects the response of the device 32 to such excitation by analyzing, for example, any harmonics which are present as determined by the acoustical energy radiated by the resonating device 32. Alternatively, the circuit 52 may analyze the decay time associated with the mechanical resonance in response to excitation by the source/detector 38. Additionally, or in the alternative, the circuit 52 may analyze other properties of the acoustic signal reradiated and/or reflected by the device 32 in response to the excitation signal (e.g., changes in the Fourier Transform of the received signal).

Features such as the presence of harmonics and/or the decay time of the received signal can be correlated to the function performed by the implant device. For example, the presence of harmonics in a stent 32 may increase or decrease as a function of the degree of restenosis which occurs within the stent. Thus, by monitoring the presence of harmonics over the course of periodic testing (e.g., trending), it is possible to track the build-up of restenosis. Similarly, a mechanical resonance decay time of the stent 32 may increase or decrease as a function of the amount of restenosis present in the stent. Still further, the system 30 can analyze other changes in the mechanical transfer function itself and correlate such changes to the amount of restenosis. The scope of the present invention is intended to encompass any and all such correlations which may be found between the parameter of interest, the acoustic excitation and the response of the device 32.

In order to interrogate/excite the stent 32 over a significant portion of its transform function frequency range, a broad band source/detector 38 is preferred. This provides for the greatest range of response and excitation of the device 32. Conventional ultrasound transducers with more limited bandwidth can also be used, although preferably after those frequencies in the mechanical transfer function of the device 32 having significant correlation to restenosis have been identified.

Figure 3:
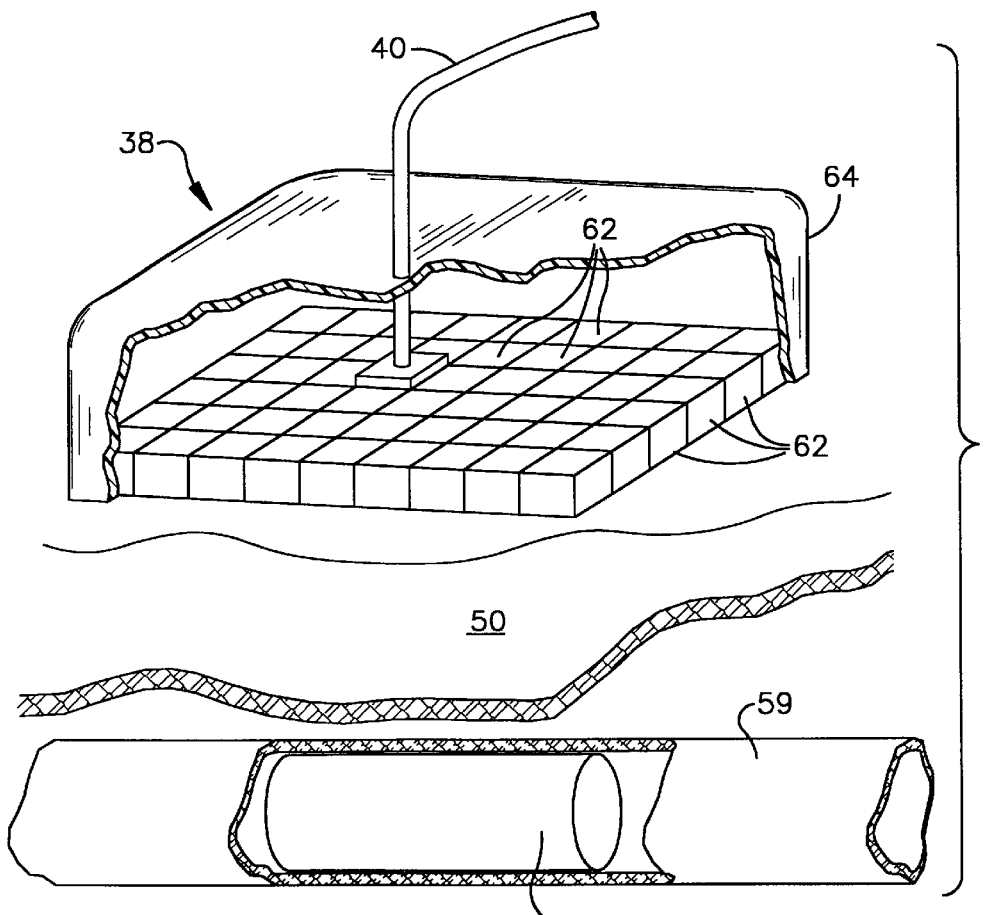
FIG. 3 is a partial schematic view representing an acoustic source/detector unit included as part of the acoustic analyzer, the source/detector unit being shown in physical proximity to an implant device being interrogated in accordance with the present invention.

FIG. 3 provides a perspective view of the source/detector 38 in relation to a stent type device 32 located in a blood vessel 59. As shown in FIG. 3, the source/detector 38 includes a two-dimensional (mxn) array 60 of miniature acoustic devices 62. Each device 62 is made up of an electro-acoustic transducer such as a piezoceramic device. In a transmit or excite mode, each device 62 is responsive to an electrical driving signal so as to emit an acoustic wave. Conversely, in a receive mode each device is designed to receive an acoustic wave and convert the received wave into an electrical signal. The level of the signal is based on the intensity of the received wave. Although the preferred embodiment utilizes an array 60 of piezoceramic devices 62, other type devices can also be used without departing from the scope of the invention.

The devices 62 are arranged in a generally planar array. The active faces of the devices 62 are oriented in a common direction so as to be directed downward towards the implant device 32. A housing 64 (shown in cut-away) provides a protective enclosure for the source/detector 38, with an acoustic window provided in the housing 64 to allow acoustic waves to be emitted and received by the devices 62.

Figure 4:
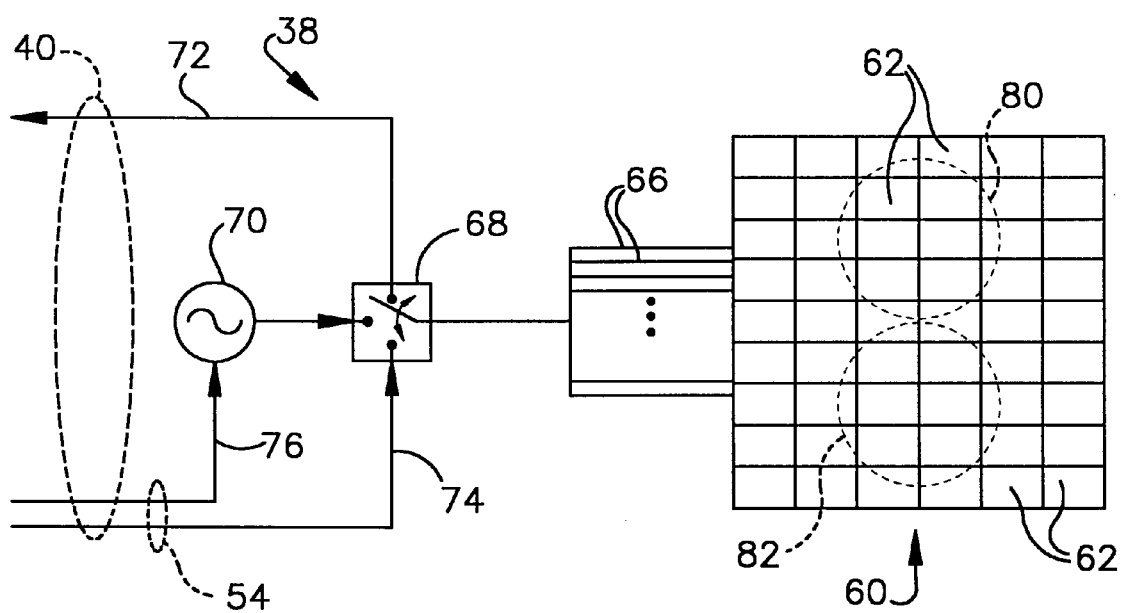
FIG. 4 is a block diagram of the source/detector unit in accordance with the present invention.

As is illustrated in FIG. 4, an electrical input/output 66 of each device 62 in the array 60 is hardwired together with the others in parallel. The input/outputs 66 are selectively connected via a switch 68 to either the output of a voltage controlled oscillator (VCO) 70 or a received signal line 72. During a transmit or excite mode, a control signal on line 74 from the circuit 52 (FIG. 2) causes the switch 68 to couple the output of the oscillator 70 to the input/output 66 of each of the devices 62. At the same time, the circuit 52 provides a control voltage on line 76 to control the frequency of the VCO 70.

Figure 5:
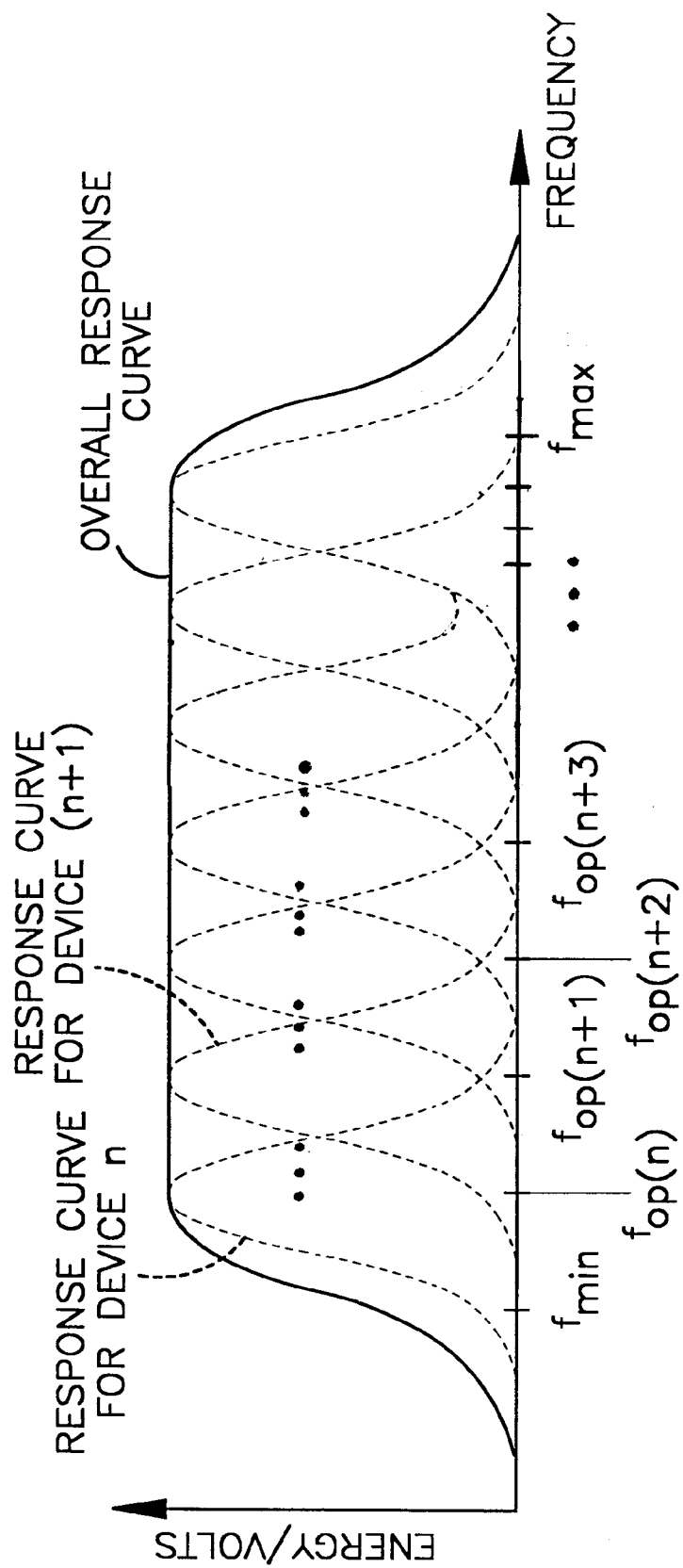
FIG. 5 is a block diagram of the broadband frequency response of the source/detector unit in accordance with the present invention.

The VCO 70 preferably is an oscillator which is designed to produce an output signal at any frequency within the acoustical range of 50 kilohertz (kHz) to 10 megahertz (MHz). Furthermore, it is desirable that each of the devices 62 provide a generally uniform response throughout the range. However, with existing piezoceramic devices 62 currently available, each device has a generally narrow band of operation (e.g., on the order of ±5% about its center operating frequency $f_{op}$). Consequently, the array 60 in the present invention is made up of devices 62 selected with different operating frequencies $f_{op}$ uniformly distributed across the broadband acoustical range of 50 kHz to 10 MHz. As a result, the composite response of the devices 62 is generally uniform as represented in FIG. 5.

In this manner, the array 60 is able to transmit and detect acoustic energy regardless of the particular frequency at which the device 32 is to be excited or at which the device 32 emits acoustic energy in response to excitation. The operating frequencies $f_{op}$ of the devices 62 are selected so that at least one device 62 is responsive to the excitation signal from the VCO 70 in order to emit an acoustic signal at each frequency. Similarly, at least one device 62 is responsive in the receive mode to detect the respective frequencies reradiated by the device 32, including any harmonics.

In a further preferred embodiment, the devices 62 with the different operating frequencies $f_{op}$ are spatially distributed within the array 60. Such spatial distribution preferably is selected so that the respective operating frequencies will be uniformly distributed across the array 60 and the overall frequency response of any region within the array 60 will be the same as the other. For example, regions 80 and 82 each preferably contain a sufficient number of devices 62 with selected operating frequencies to exhibit the same response curve shown in FIG. 5. Therefore, it will be appreciated that the overall array 60 will function as a broadband source/detector generally independent of the particular region (e.g., 80 or 82) which is positioned immediately adjacent the device 32. The array 60 therefore will be operative throughout the entire acoustic frequency band of interest.

Briefly referring back to FIG. 3, the stent device 32 may be a conventional stent which generally consists of a cylindrical tube. The tube may be made of metal such as stainless steel, or another material such as plastic and/or a composite material. The tube wall may be uniform, helical, or some other geometry.

Notably, the stent 32 will have a resonant frequency $\omega_R$ (or frequencies in the case of there being multiple resonant frequencies), based upon its physical configuration and material properties of the stent 32. The inventors have recognized that if the stent 32 is excited by an acoustic pulse which has strong frequency component(s), $\omega_P$, of its own in the neighborhood(s) of the resonant frequency or frequencies $\omega_R$, the reradiated signal of the stent 32 will contain both sets of frequency components (i.e., $\omega_P$ and $\omega_R$), and that the amplitude of these components, both absolutely and relative to one another, will be a function of the degree of damping of the sent 32 due to restenosis. FIG. 7a is an example of such a function: It is a plot of the amplitude of the resonance frequency componet, $\omega_R$, as a function of damping coefficient "a".

Figure 7B:
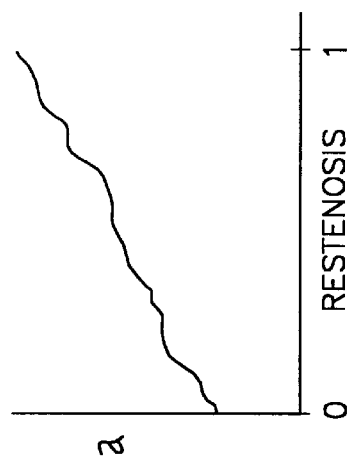
FIG. 7b is a graph illustrating a variation in the damping constant of a stent as a function of degree of restenosis in accordance with the present invention.
Figure 7A:
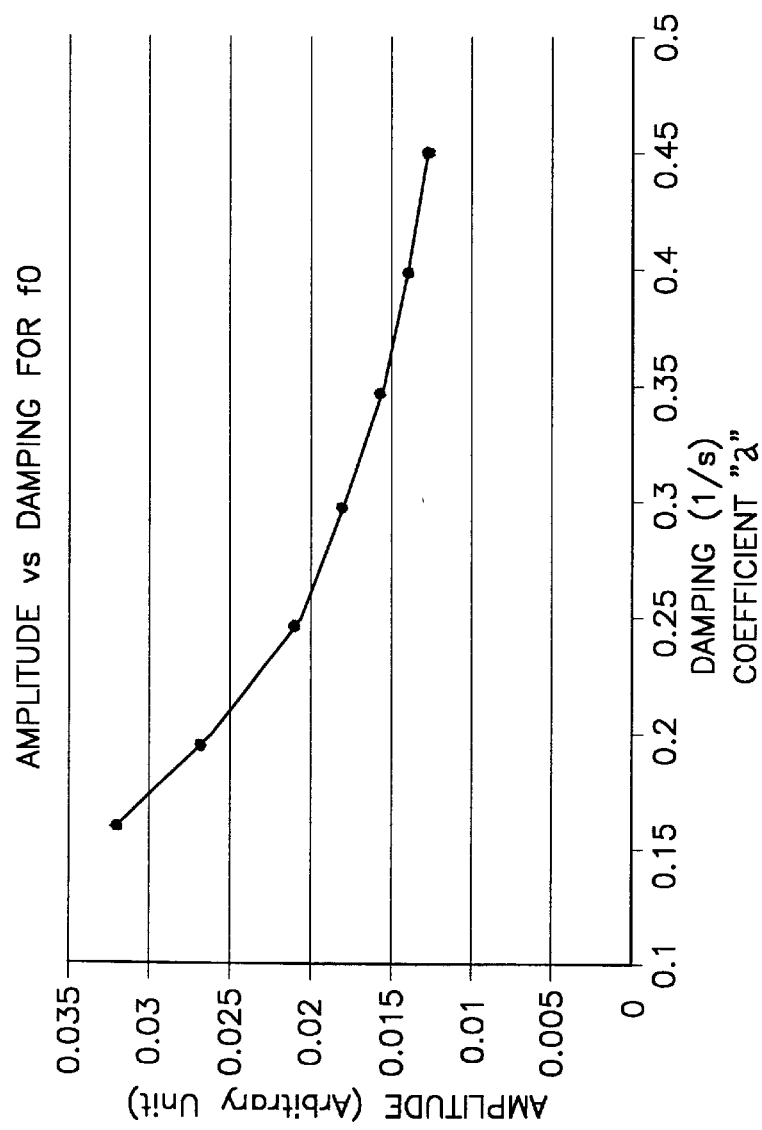
FIG. 7a illustrates a relationship between the degree of damping of a stent due to restenosis and the amplitude of an acoustic signal received from a stent.

FIG. 7b illustrates how the damping coefficient "a" varies with respect to degree of restenosis. In FIG. 7b, a level 0 restenosis represents no occlusion in the stent and the damping coefficient a is at a local minimum. A level 1 restenosis represents complete occlusion at which the damping coefficient a is at a local maximum. Thus, the stent 32 can be said to have a mechanical transfer function which varies in relation to the degree of restenosis.

The amplitude distribution of the reradiated signal from the stent 32 in the frequency domain can be found from the Fourier transform of the reradiated signal.

Thus, if a time domain measurement of the reradiated acoustic energy from the stent 32 is made and then Fourier transformed so that the power or amplitude at the frequency or frequencies $\omega_R$ is determined, then the damping coefficient a can be determined from FIG. 7a mentioned above, for example. The amount of occlusion or degree of restenosis can then be estimated via the correlation represented in FIG. 7b.

Figure 6:
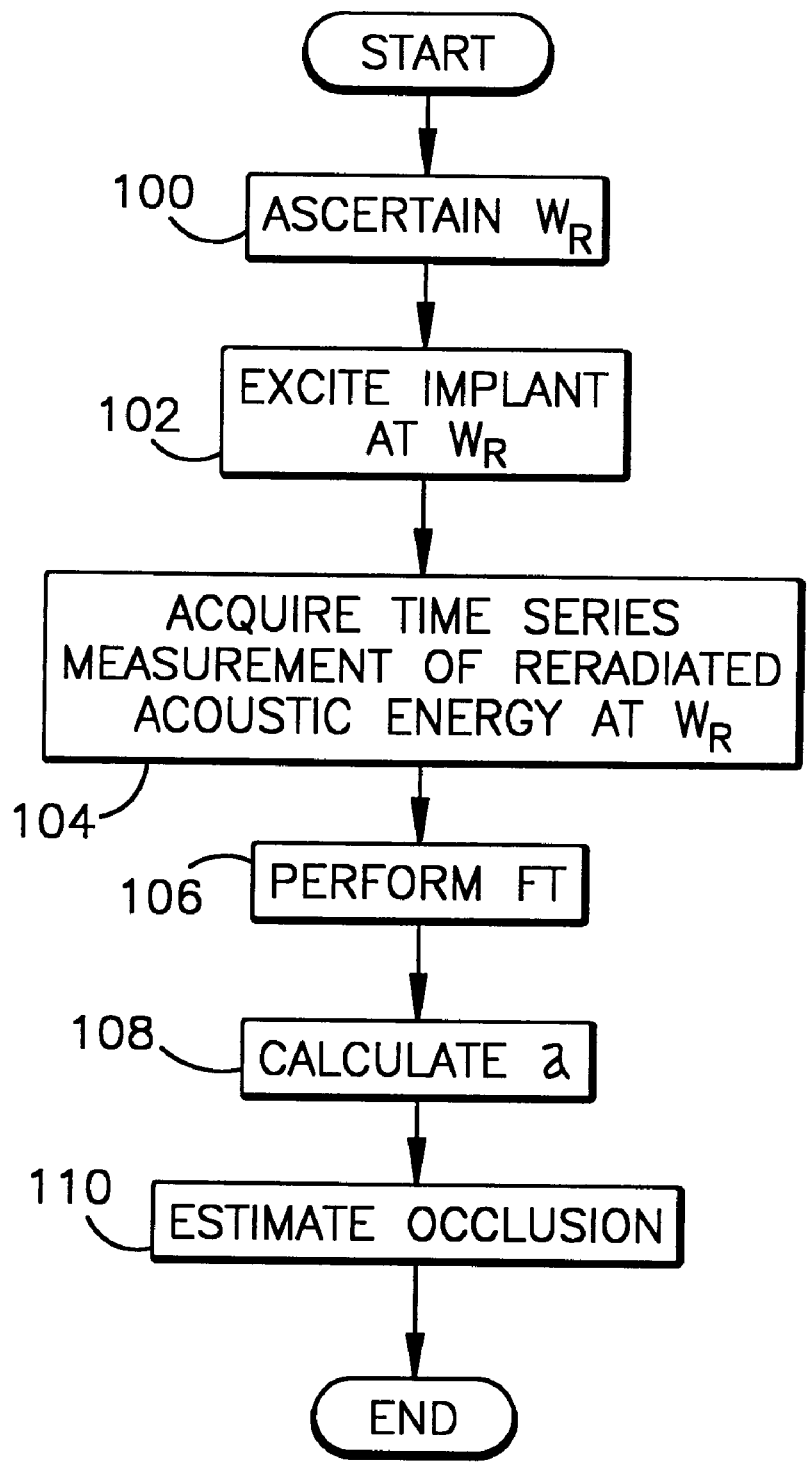
FIG. 6 is a flowchart illustrating steps for interrogating a stent to estimate restenosis according to one embodiment of the present invention.

FIG. 6 is a flowchart representing the above analysis as carried out by the system 30 in accordance with one embodiment of the invention. The data processing and control circuit 52 (FIG. 2) includes a microprocessor which is programmed to carry out the appropriate control and processing described herein. Such programming will be apparent to those having ordinary skill in the art based on the disclosure provided herein. Hence, further details regarding the particular programming have been omitted for sake of brevity.

Beginning in step 100, the system 30 initializes itself by ascertaining the most suitable resonant frequency $\omega_R$ of the stent 32. In one embodiment this may be done by reference to a lookup table of resonances for different stents (e.g., known commercially available stents). Such data can be previously obtained empirically in laboratory tests. Alternatively, the source/detector unit 38 is held in close proximity to the patient's body with the array 60 facing the stent 32 (e.g., as represented in FIG. 1). The control circuit 52 (FIG. 2) systematically begins to sweep the output frequency of the VCO 70 through the acoustic frequency band in which the resonant frequency $\omega_R$ is expected to appear. The output of the VCO 70 is applied to the array so that the stent 32 is excited by the acoustic energy at the frequency of the VCO 70. The circuit 52 systematically samples the acoustic energy which is reradiated by the stent 32 at each frequency by controlling the switch 68. The energy level of the reradiated signal at each particular frequency is input to the circuit 52 from the signal conditioning circuit 58.

Since the source/detector 38 is preferably broadband as noted above, at least one device 62 is operative at each frequency to transmit and receive the acoustic signal. The circuit 52, in step 100, determines at which frequency in the acoustic frequency band the reradiated acoustic energy is at its highest level as detected by the source/detector 38. Such maximum energy frequency level will correspond to the most suitable resonant frequency $\omega_R$ of the stent 32, typically, and thus the circuit 52 ascertains the resonant frequency $\omega_R$.

Next, in step 102, the circuit 52 causes the source/detector 38 to excite the stent 32 with a brief burst of acoustic energy at or near the resonant frequency $\omega_R$. The signal received from the stent 32 is input to the circuit 52 from the conditioning circuit 58. The circuit 52 then proceeds to take a time series measurement of the reradiated acoustic energy signal from the stent 32 as represented in step 104.

Next, the circuit 52 takes the Fourier transform of the time series data in step 106. The Fourier transform yields, among other things, the energy components of the reradiated acoustic energy at the frequencies $\omega_R$. Using a lookup table based on an empirically determined curve like that shown in FIG. 7a, for example, the circuit 52 determines the damping coefficient "a" in step 108. The circuit 52 then compares the value of the damping coefficient "a" with a table stored in memory representing the graph of FIG. 7b, for example. Based on the value of "a", the circuit 52 estimates the degree of restenosis as represented in step 110. The circuit 52 may then provide an output on the display 44 or the like indicating such estimate. Moreover, the circuit 52 may store such information in memory for future use in trending or the like.

In an alternate embodiment, the circuit 52 may use other known data analysis techniques to analyze the frequency content of the acoustic energy reradiated from the stent 32. For example, wavelet transformations and/or neural network techniques may be employed by the control circuit. Moreover, such techniques may be modified to account for different conditions in taking the measurements such as large muscle mass, nearby bone structures, etc.

Additionally, the circuit 52 may employ such techniques as pattern recognition to analyze the reradiated acoustic energy. For example, the circuit 52 may be programmed to carry out pattern recognition to analyze the class of resonant frequencies exhibited by the stent 32 in response to the acoustic excitation.

FIGS. 8 and 9 illustrate a specially designed acoustic reradiating stent 120 which can be substituted for the otherwise conventional stent 32 described above. The stent 120 is made up of two hollow concentric cylinders 122 and 124 which are mechanically connected so that the entire structure has a pronounced mechanical resonance at a resonant frequency $\omega_R$ within the acoustic frequency band. The outer cylinder 122 and the inner cylinder 124 are each made of a biocompatible material such as stainless steel, plastic, etc.

The outer cylinder 122 is mechanically connected to the inner cylinder 124 by resilient connecting members 126. The connecting members 126 are made of a resilient material such as rubber or plastic. Each member 126 is sufficiently rigid to maintain generally a physical separation between the two cylinders, yet is sufficiently resilient to allow for relative movement between the cylinders 122 and 124 at the resonant frequency $\omega_R$. In the exemplary embodiment, the connecting members 126 are equally spaced around the circumference of the cylinders. However, it will be appreciated that other configurations are also possible.

The stent 120 further includes a seal ring 128 at each end which seals off the circumferential area between the two cylinders 122. The seal rings 128 prevent blood from entering the area between the cylinders. The seal rings 128 are made up of a resilient material such as rubber or plastic similar to the connecting members 128.

Hence, the stent 120 will exhibit a pronounced mechanical resonance based on the relative motion which can occur between the two concentric cylinders.

The stent 120 may be utilized in accordance with the system 30 as described in relation to FIG. 6. In particular, the damping coefficient may be determined from a curve like that shown in FIG. 7a and used to estimate occlusion as described above. In an alternative embodiment, however, the degree of restenosis may be estimated using a different, albeit related, criteria.

For example, FIG. 10 illustrates represents a configuration of the system 30 in which the decay time of the reradiated acoustic energy is utilized to estimate restenosis. More particularly, the stent 120 is excited at or near its resonant frequency or frequencies $\omega_R$ in a manner similar to that described above in steps 100 and 102 in FIG. 6. Upon switching the switch 68 from excite mode to receive mode, the array 60 is then used by the circuit 52 to detect the acoustic energy reradiated from the stent 120 at the resonant frequency(s) $\omega_R$.

Figure 12B:
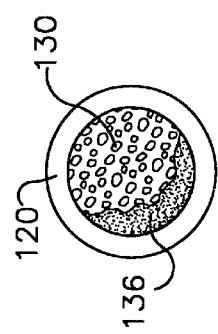
FIGS. 12a and 12b are cross-section views illustrating a stent with different degrees of restenosis.
Figure 12A:
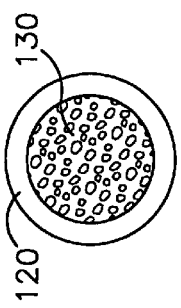
Figure 11B:
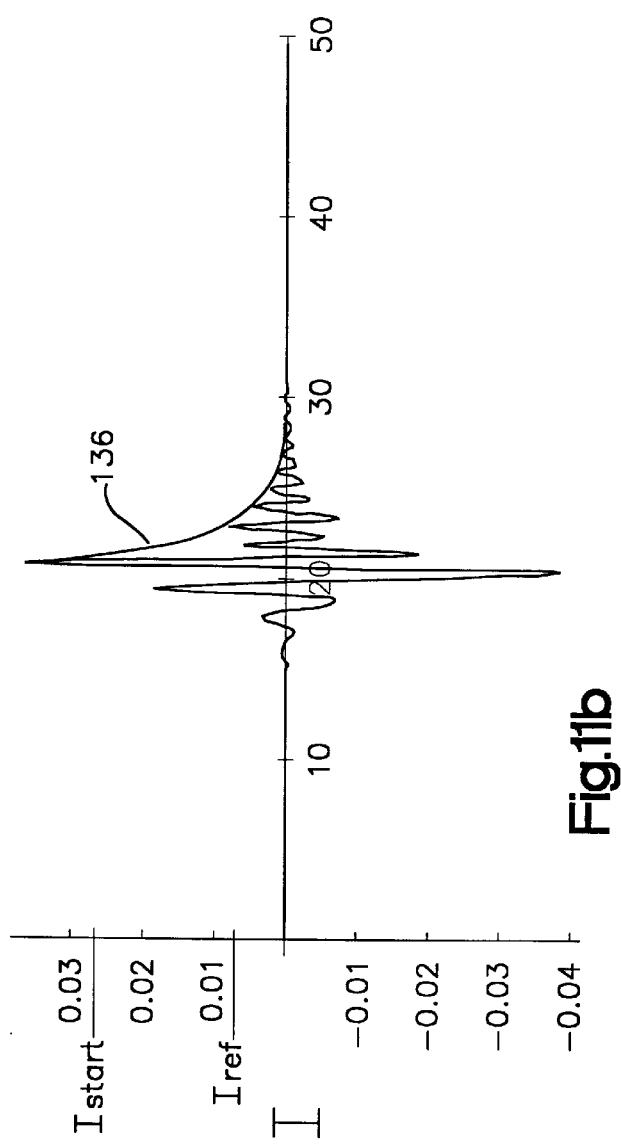

Specifically, the circuit 52 measures the amplitude of the reradiated acoustic energy over time in order to determine its decay time. With no restenosis, and hence little or no damping, the cross section of the stent 120 will be filled with blood 130 as represented in FIG. 12a. The non-occluded stent 120 will have a characteristic decay time following excitation as represented by curve 134 in FIG. 11a. As restenosis proceeds, the non-blood tissue 136 will begin to fill the cross section of the stent 120 as shown in FIG. 12b. Depending on the particular design of the stent 120, the restenosis build-up will modify the decay time of the reradiated acoustic energy.

In the exemplary embodiment, the stent 120 varies in decay time as a a function of increasing restenosis. Thus, the decay time may decrease as restenosis increases as represented by curve 136 in FIG. 11b. By comparing the decay time of the reradiated acoustic energy from a given energy level $I_{start}$ to a second level $I_{ref}$, the circuit 52 is programmed to estimate the degree of restenosis. Such estimate can be based on expected values stored in the circuit 52. In addition, or in the alternative, the measured decay time can be stored in memory in the circuit 52 for purposes of trending.

It will be appreciated that several inventive aspects have been described herein with respect to a stent 32 or 120. Nevertheless, it will be further appreciated that the same inventive aspects apply to other medical implant devices such as grafts, orthopedic prostheses, orthopedic trauma implants and reinforcements, etc. While analyzing the acoustic energy reradiated by the device is described in connection with determining the amount of restenosis, it will be appreciated that other parameters may also be determined. For example, frequency content changes, variations in the decay time, phase shifts, etc., can be utilized by the circuit 52 to estimate stress, strain, boundary constraints, etc., within and on the device. Provided the transfer function of the device 32 can be determined in relation to a parameter of interest, the present invention allows such information to be obtained remotely from the implanted device using acoustic energy.

Figure 13:
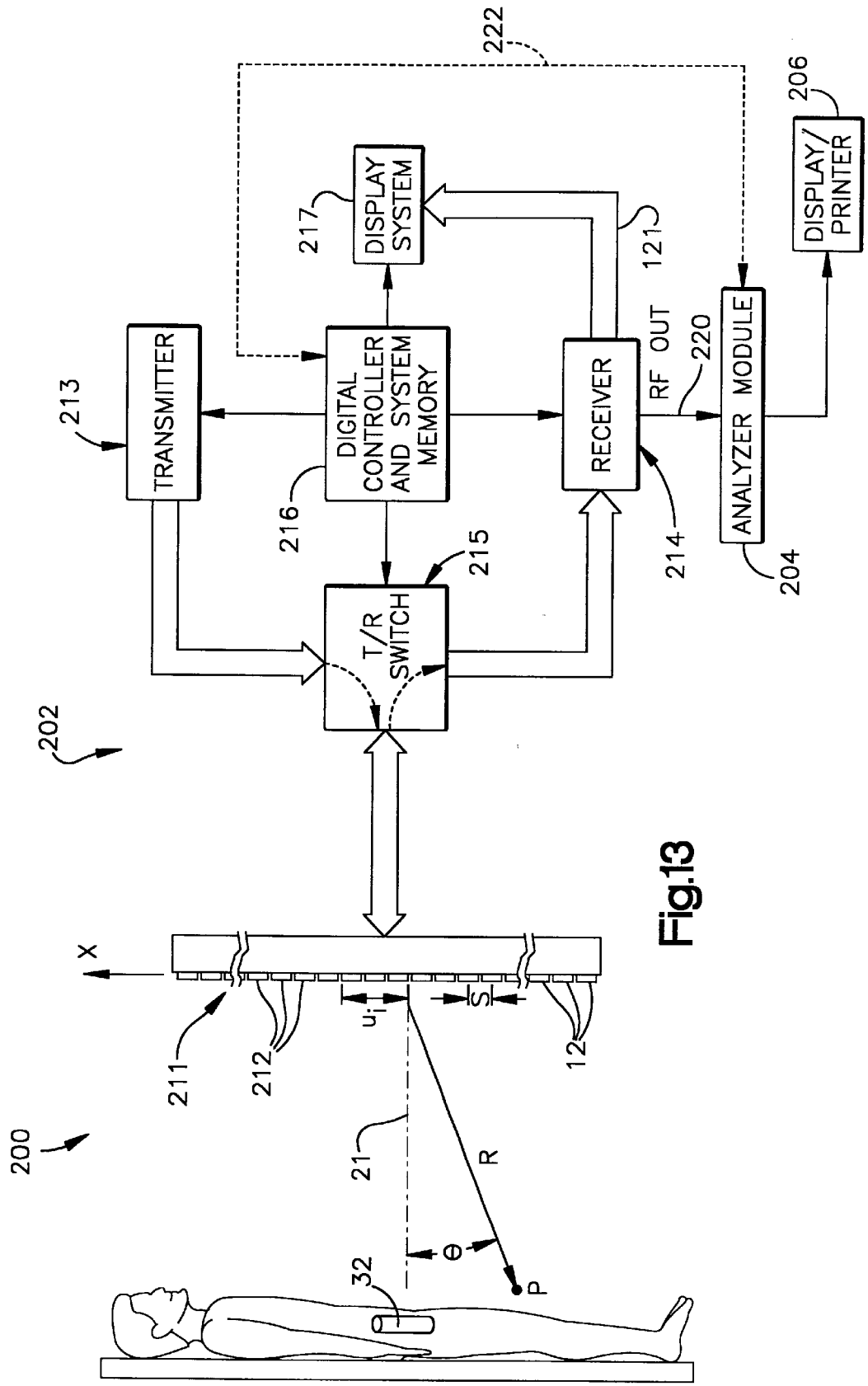
FIG. 13 is a block diagram illustrating another embodiment of a system in accordance with the present invention in which an analyzer module is added on to a conventional ultrasonic imaging apparatus.

Referring now to FIG. 13, another embodiment of a system according to the present invention is shown for diagnosing restenosis in a stent. However, it will be appreciated that the same techniques can be applied to other medical implant devices in the same manner referred above. The system 200 shown in FIG. 13 comprises a conventional ultrasonic imaging apparatus 202 in combination with an analyzer module 204 and optional display/printer 206.

As will be discussed in more detail, the ultrasonic imaging apparatus 202 provides ultrasonic data to the analyzer module 204. The analyzer module 204 captures and digitizes the data, and performs one or more analyses in order to determine the degree of restenosis which has built up in a stent 32 implanted within a living body. The analyzer module 204 may actively control the imaging apparatus 202, or function merely to acquire the data and perform post-acquisition processing and analysis as is discussed below.

The exemplary ultrasonic imaging apparatus 202 includes a transducer array 211 comprised of a plurality of separately driven elements 212 which each produce a burst of ultrasonic energy when energized by a pulsed waveform produced by a transmitter 213. The ultrasonic energy reflected and/or reradiated back to transducer array 211 from the subject under study (e.g., the stent 32 located within the living body as shown in FIG. 1) is converted to an electrical signal by each transducer element 212 and applied separately to a receiver 214 through a set of transmit/receive (T/R) switches 215. Transmitter 213, receiver 214 and switches 215 are operated under control of a digital controller and system memory 216 responsive to commands by a human operator. A complete scan is performed by acquiring a series of echoes in which switches 215 are set to the transmit position, transmitter 213 is gated on momentarily to energize each transducer element 212, switches 215 are then set to the receive position, and the subsequent echo signals produced by each transducer element 212 are applied to receiver 214. The separate echo signals from each transducer element 212 are combined in receiver 214 to produce a single echo signal which is employed to produce a line in an image on a display system 217.

The transducer array 211 typically has a number of piezoelectric transducer elements 212 arranged in an array and driven with separate voltages (apodizing). By controlling the time delays (or phase) and amplitude of the applied voltages, the ultrasonic waves produced by the piezoelectric elements 212 (transmission mode) combine to produce a net ultrasonic wave that travels along a preferred beam direction and is focused at a selected point along the beam. By controlling the time delays and amplitude of successive applications of the applied voltages, the beam with its focal point can be moved in a plane to scan the subject. Likewise, by controlling the time delays, etc., the beam in accordance with the present invention can be directed at different angles and depths relative to the living body in order to focus the ultrasonic radiation on a particular object, namely the stent 32.

The same principles apply when the transducer array 211 is employed to receive the reflected sound (receiver mode).

That is, the voltages produced at the transducer elements 212 in the array 211 are summed together such that the net signal is indicative of the sound reflected from a single focal point in the subject e.g., the location of the stent 32 in accordance with the present invention). As with the transmission mode, this focused reception of the ultrasonic energy is achieved by imparting separate time delays (and/or phase shifts) and gains to the signal from each transducer array element 212. In addition, to reduce side lobes in the receive beam the amplitude of each transducer element signal is modified in accordance with a window function prior to summation into the focused beam. Suitable ultrasonic imaging apparatuses 202 are described in more detail in U.S. Pat. No. 5,345,939, for example, the entire disclosure of which is incorporated herein by reference.

In the exemplary embodiment, the receiver 214 provides an RF output signal on line 220 which represents the net signal indicative of the sound reflected from the single focal point. Thus, when the ultrasonic beam is properly focused on the stent 32 by virtue of a doctor, nurse or medical assistant positioning the hand-held sized transducer array 211 outside the body of the patient 34 in close proximity to the implant device 32 and adjusting the position and focus of the beam, the signal on line 220 represents the ultrasonic signal reflected back and/or reradiated by the stent 32. Likewise, when the ultrasonic beam from the transducer array 211 is focused on another portion of the living body (e.g., the heart), the signal on line 220 represents the acoustic energy reflected or reradiated by that particular portion of the body.

The RF output signal on line 220 is input to the analyzer module 204 as shown in FIG. 13. The analyzer module 204 captures the received ultrasonic signal and digitizes the signal to produce data which is then processed in order to evaluate predefined parameters associated with the stent 32 such as the amplitude, frequency response, decay times, etc. The analyzer module 204 uses the measured parameters to determine the degree of restenosis experienced by the stent 32 based on predefined conditions, a neural network, expert system, or the like programmed into the analyzer module 204 via software, etc. The result(s) of the diagnos(es) are then provided by the analyzer module 204 to the display/printer 206 so that they may be observed or recorded by the operator. In addition, or in the alternative, the results of the analysis may be stored in memory by the analyzer module 204 together with the received data itself, for example, for future reference, trending, etc.

In the exemplary embodiment, the analyzer module 204 is coupled to the digital controller 216 via an optional interface connection represented by phantom control bus 222. As will be discussed below in relation to FIG. 14, the analyzer module 204 includes an interface which allows the analyzer module 204 to control the ultrasonic imaging apparatus 202 remotely with respect to parameters such as frequency, amplitude and location of the ultrasonic beam transmitted/received by the transducer array 211. This allows the analyzer module 204 to adjust automatically such parameters when interrogating the stent 32. Alternatively, the analyzer 204 may be programmed to output instructions on the display 206 to prompt an operator to provide various adjustments of the ultrasonic beam with respect to frequency, amplitude, location, etc. via the controls provided with the conventional apparatus 202.

Figure 14:
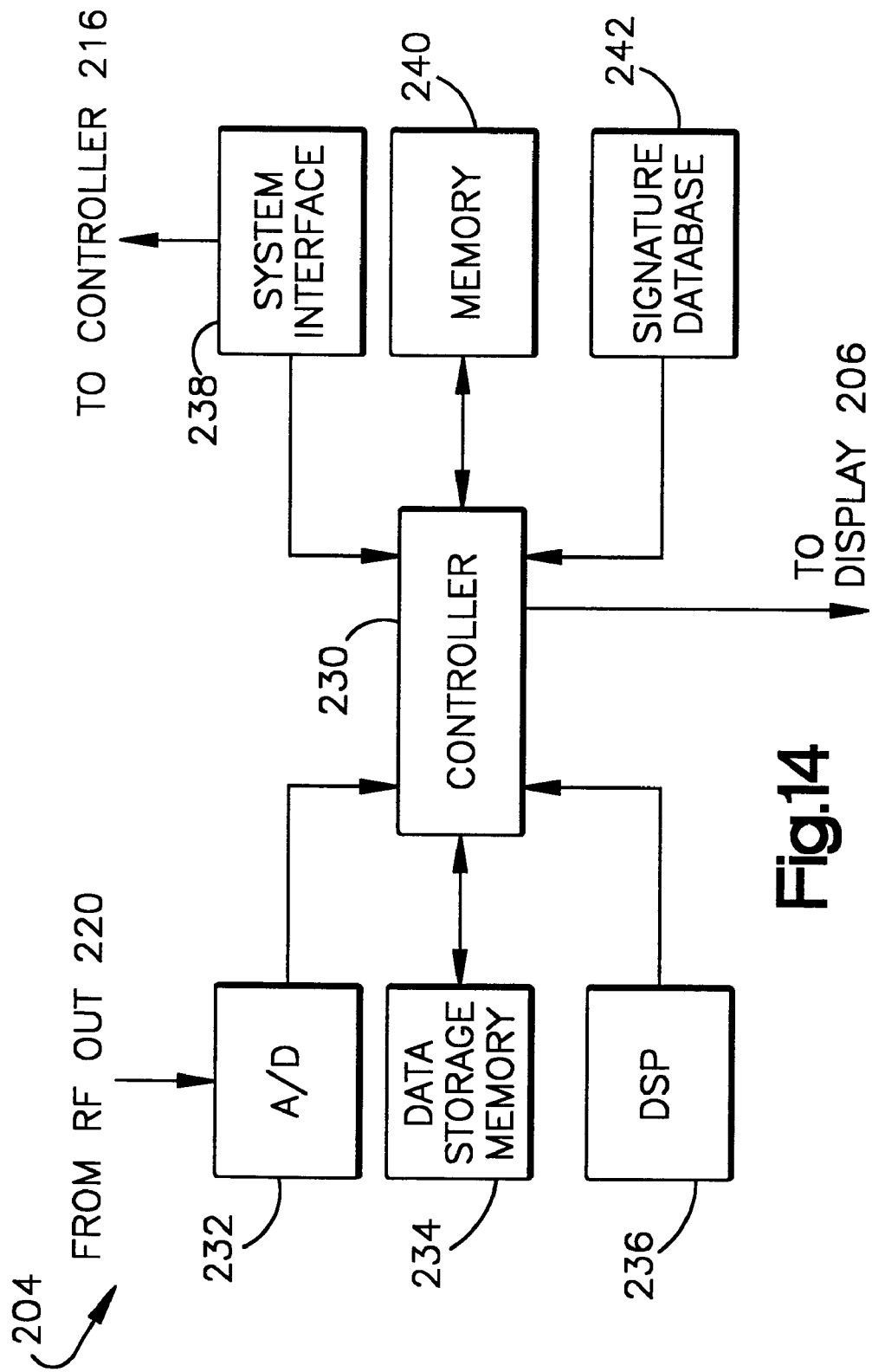
FIG. 14 is a block diagram of the analyzer module in accordance with the present invention.

Turning now to FIG. 14, the analyzer module 204 is shown in detail. The analyzer module 204 includes a controller 230 which is programmed to carry out and/or coordinate performance of the various functions described herein. In addition, the analyzer module 204 includes an analog-to-digital (A/D) converter 232 which receives the RF output signal on line 220 and digitizes the signal for subsequent processing. Data storage or buffer memory 234 such as a hard drive or the like is provided for storing the digitized data received via the RF output signal. The analyzer module 204 further includes a digital signal processor (DSP) 236 for carrying out high speed math computations such as FFTs, wavelet transforms, etc. in order to analyze the data stored in the data storage memory 234.

A system interface 238 enables the controller 230 to communicate with the digital controller 216 via control bus 222 in the preferred embodiment. As noted above, the interface 238 in the preferred embodiment allows the controller 230 within the analyzer module 204 to control the ultrasonic imaging apparatus 202 remotely with respect to parameters such as frequency, amplitude and location of the ultrasonic beam transmitted/received by the transducer array 211. A memory 240 is included in the analyzer module 204 for serving as working memory as well as storing computer programming code designed to be executed by the controller 230 and/or DSP 236 for carrying out the operations described herein. The particular programming code can be written in any of a variety of conventional programming languages by those having ordinary skill in the art based on the disclosure provided herein. Accordingly, further detail on the particular programming code is omitted for sake of brevity.

The memory 240 may include random access memory together with non-volatile memory. The memory 240 may include more permanent storage such as a hard drive, disc drive, etc., as will be appreciated. The program for carrying out the functions described herein is stored in computer readable format within the memory 240 and is accessed and executed by the controller 230 and/or DSP 236 in order carry out such functions.

A signature database 242 is also included in the analyzer module 204. The signature database 242 stores signature data associated with one or more known medical devices such as commercially available stents. The signature data may include data describing the mechanical transfer function of the respective stents in relation to their response to ultrasonic radiation of the type provided by the system 200. For example, the signature database 242 may include frequency response information for different type stents as discussed below in relation to FIG. 19. Such signature data may be obtained empirically, based on modeling, etc. The signature data can be stored with respect to different types of stents which are free of occlusion. In addition, the signature data may include data for each stent representing different degrees of occlusion, for example.

It will be appreciated that the analyzer module 204 may easily be incorporated into a personal computer or other device which is coupled to the ultrasonic imaging apparatus 202. Hence, with the addition of a relatively small amount of additional hardware and software programming running within the analyzer module 204, the system 200 of the present invention can make use of existing ultrasonic imaging apparatus equipment. This allows hospitals and other healthcare facilities to maximize use of their available resources. In the alternative, it will be appreciated that the system 200 could be configured and sold as an integral unit without departing from the scope of the invention.

Figure 15A:
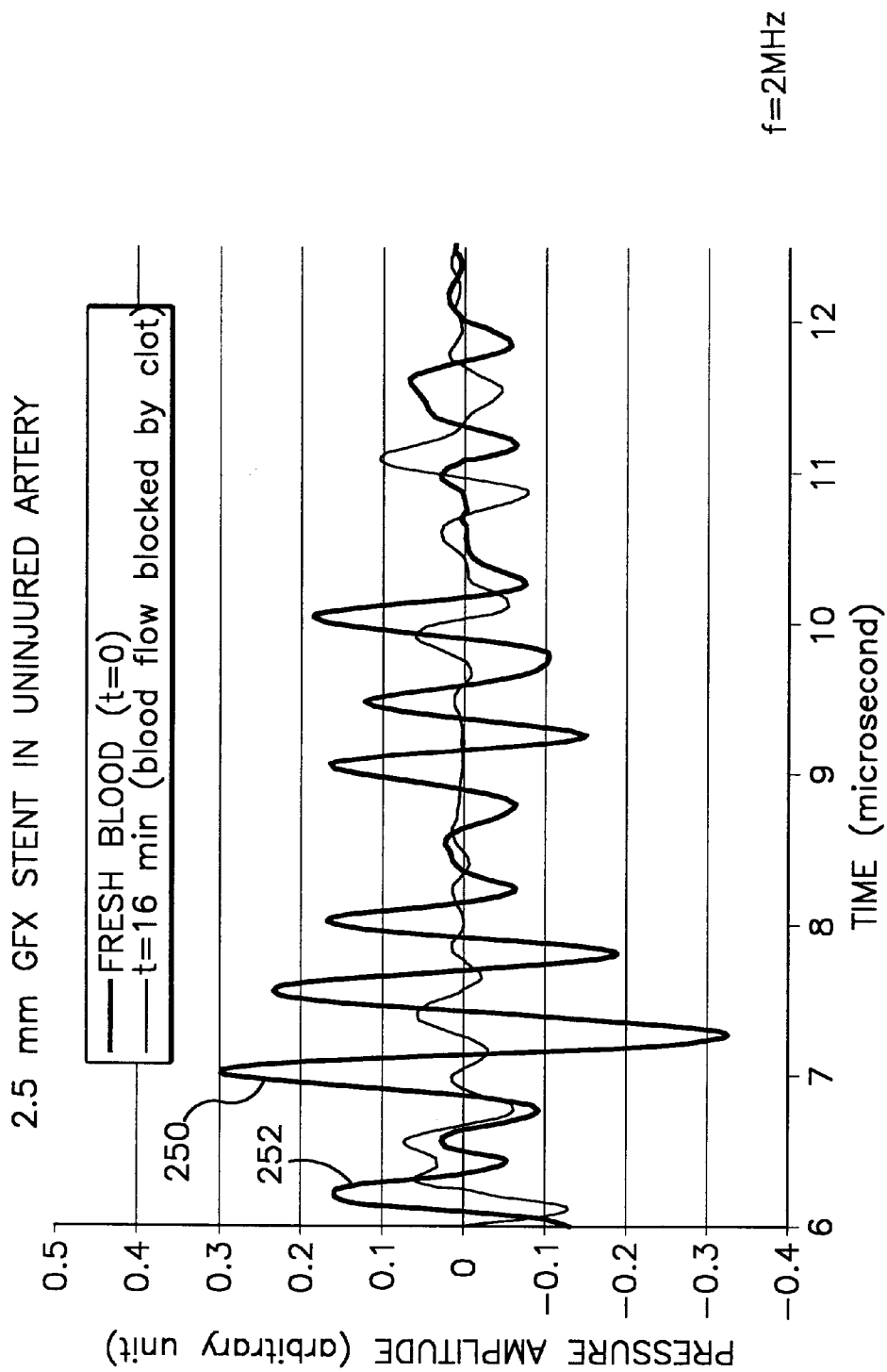

Referring now to FIG. 15a, provided is an example of how the amplitude of the reflected ultrasonic signal from a stent 32 varies as a function of the amount of restenosis which has built up within the stent. FIG. 15a represents data which was obtained at an ultrasonic frequency of 2 megahertz (MHz) for a 2.5 millimeter (mm) stent in an uninjured artery from a pig. The vertical axis represents the amplitude of the reflected signal (arbitrary units). The horizontal axis represents time in microseconds following the respective stents being excited by an ultrasonic pulse at 2 MHz.

Line 250 in FIG. 15a illustrates the response of a clean stent 32. Line 252 represents the response of the same type stent 32 which has incurred a buildup of thrombus in which blood flow was completely blocked after 16 minutes. As is shown in FIG. 15a, the amplitude of the ultrasonic signal received from the stent 32 is significantly reduced by the thrombus. FIG. 15b illustrates the FFT of each of lines 250 and 252 (designated 250F and 252F, respectively). As can be seen, the FFTs differ markedly for the two states.

Figure 15C:
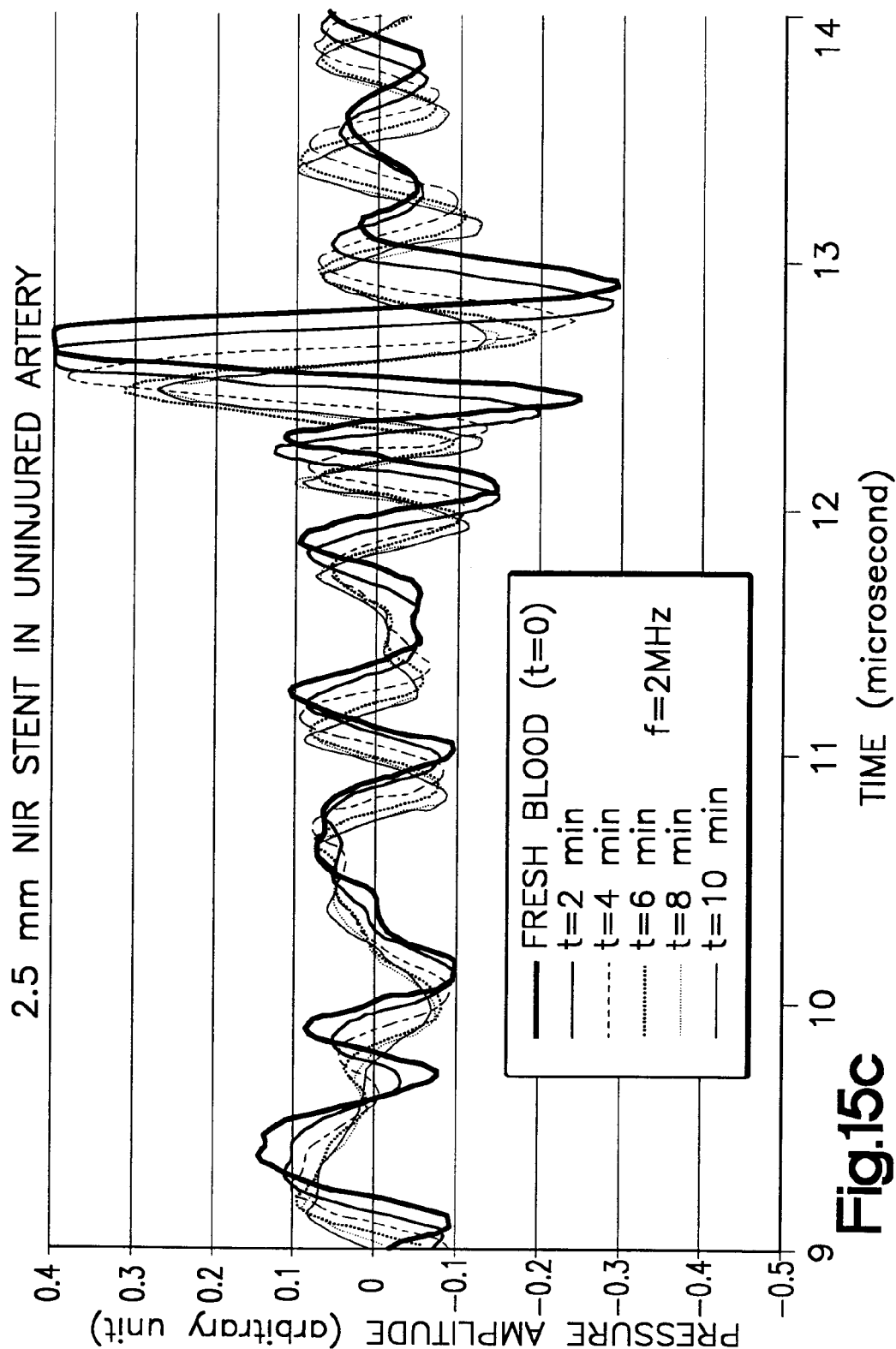

Similar information is illustrated in FIG. 15c for a 2.5 mm NIR stent 32 at various degrees of restenosis. As the amount of restenosis increases, the amplitude of the response signal tends to decrease.

Information such as that shown in FIGS. 15a, 15b and 15c is programmed into the analyzer module 204 in order to diagnose the amount of restenosis experienced by a stent 32 under study. Such information may include absolute or relative amplitudes with respect to time, frequency, etc., decay times as is discussed above in connection with the previous embodiment, harmonics, etc. Stored within the analyzer module 204 is a set of rules, predefined conditions, etc. against which the ultrasonic data received by the analyzer module 204 from the stent 32 under test can be compared and the analyzer module 204 compares the data so as to reach a conclusion. For example, if the relative amplitudes at different times for a particular type of stent 32 change by a predetermined fraction, the analyzer module 204 concludes that the stent 32 has undergone an X% occlusion due to restenosis. Alternatively, if the frequency components of the received ultrasonic signal at one or more excitation frequencies change by a predefined amount, the analyzer module 204 concludes that there is Y% occlusion, for example. Generally speaking, the analyzer module 204 extracts the parameters of interest from the received signal and calculates appropriate figures of merit which correlate with clinical evidence of restenosis. Such information can then be displayed via the display 206 or the like.

Data such as that shown in FIGS. 15a, 15b and 15c can also be stored in the signature database 242 as signature patterns against which the analyzer module 204 can compare measured ultrasonic data from a stent 32 within a living body. It will be appreciated that the DSP 236 may be tasked by the controller 230 to carry out the complex math functions (e.g., FFTs, pattern matching, etc.) associated with the various desired analyses at high speed using conventional techniques. Each of the respective components within the analyzer module 204 are configured to be able to access the appropriate data from the other components as needed again using conventional techniques.

Figure 16:
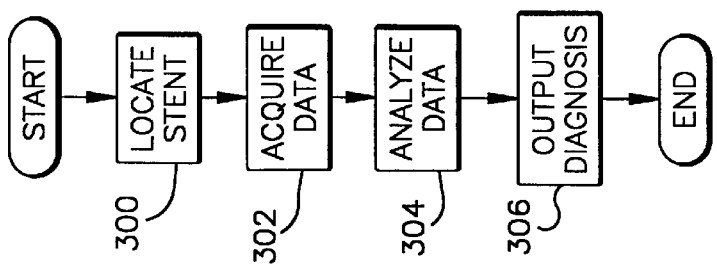
FIG. 16 is a flowchart suitable for programming the system to acquire and analyze data from a stent in accordance with the present invention.

Referring now to FIG. 16, shown is a flowchart illustrating the general operating process of the system 200 in accordance with the present invention. An operator begins the procedure by placing the transducer array 211 on the body of the patient in proximity to the implanted stent 32. In step 300, the precise location of the stent 32 within the body is determined in order to ensure that the ultrasonic beam from the transducer array 211 is incident thereon. Step 300 may be carried out automatically as described below in connection with FIG. 17, or manually as discussed below in connection with FIG. 18, for example.

Upon locating the stent 32, the system 200 proceeds to step 302 in which the stent 32 is irradiated with ultrasonic energy from the transducer array 211. The reflected/reradiated energy from the stent 32 is received by the transducer array 211 and the resultant RF output signal is provided to the analyzer module 204. The analyzer module 204 may control the particular frequenc(ies), amplitude(s), etc. of the ultrasonic beam automatically via the control bus 222 (FIG. 13), or simply prompt the operator to set the appropriate parameters via the display 206 or the like. The analyzer module 204 in step 302 captures and digitizes the data via the A/D converter 232, and stores the data in the data storage memory 234.

In step 304, the analyzer module 204 performs preprogrammed routines for analyzing the acquired data such as taking the FFT, wavelet transformations, etc. The analyzer module 204 uses such information in the manner described above in order to assess the extent of restenosis experienced by the stent 32. Next, in step 306 the analyzer module 204 outputs the diagnosis via the display 206 or the like.

Figure 17:
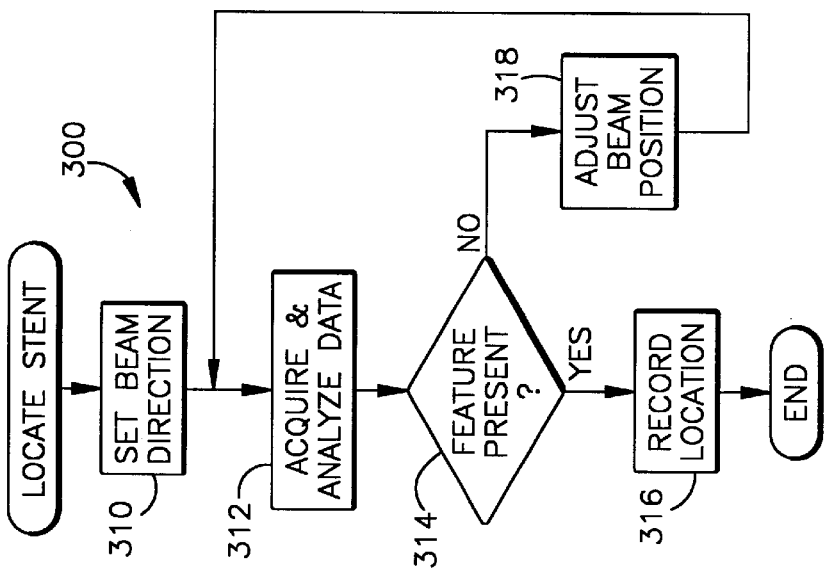
FIG. 17 is a flowchart suitable for programming the system to locate a stent in accordance with one embodiment of the present invention.

FIG. 17 illustrates an automated embodiment for locating a stent 32 within the body in accordance with the present invention. Once the transducer array 211 has been placed outside the body in close proximity to the stent 32 by the operator in step 300, the controller 230 within the analyzer module 204 provides control commands to the controller 216 in the imaging apparatus 202 to direct and receive the ultrasonic beam to/from the location of the stent 32. For example, the ultrasonic beam is first set to an initial location (e.g., θ=0°) as shown in step 310. The analyzer module 204 then acquires and analyzes the ultrasonic data received from such location in step 312. In step 314, the analyzer module 204 determines whether the data acquired in step 312 includes a characteristic feature indicative of the presence of the stent 32. For example, the stent 32 may be known to exhibit a substantial resonance at a particular frequency, such resonance not being exhibited by other portions of the body.

If in step 314 the characteristic feature is detected as determined by the analyzer module 204, the location of the beam is noted and fixed via the control bus 222 as represented in step 316. On the other hand, if the characteristic feature is not detected in step 314, the analyzer module 204 proceeds to step 318 wherein it causes the controller 216 to adjust the location of the ultrasonic beam and the process returns to step 312. Accordingly, the location of the ultrasonic beam may be adjusted incrementally in steps 312, 314 and 318 based on a predefined pattern, for example, until the precise location of the stent 32 is determined.

Figure 18:
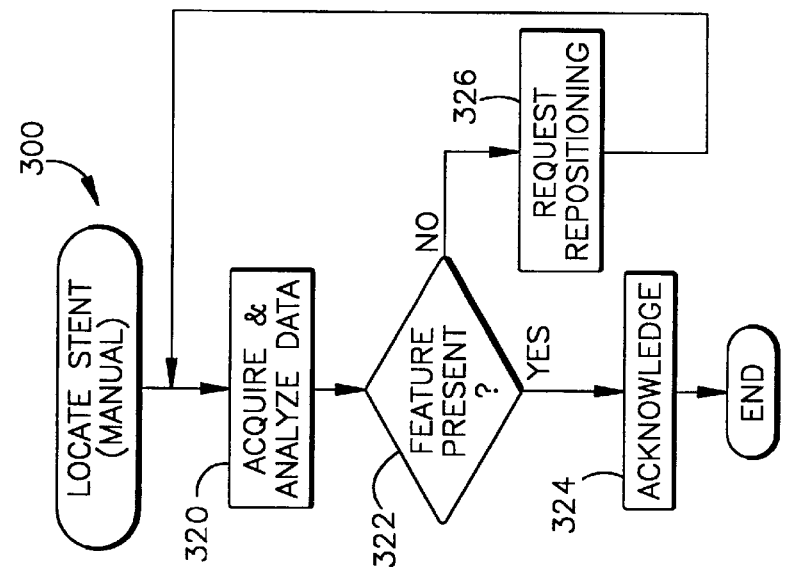
FIG. 18 is a flowchart suitable for programming the system to locate a stent in accordance with another embodiment of the present invention.

FIG. 18 illustrates an embodiment of step 300 which is carried out semi-manually. The imaging apparatus 202 is configured such that the ultrasonic beam position as transmitted/received by the transducer array 211 is fixed (e.g., θ=0°). After the operator has placed the transducer array 211 proximate the stent 32 on the body, the analyzer module 204 is configured to acquire and analyze the ultrasonic data in step 320 similar to step 312. Next, in step 322 the analyzer module 204 determines if the predefined characteristic feature is present in the received data similar to step 314. If yes, the analyzer module 204 in step 324 displays an acknowledgment to the operator on the display 206 to instruct the operator to maintain the present position of the transducer array 211. If no in step 322, the analyzer module 204 in step 326 displays a request on the display 206 that the operator adjust the location of the transducer array 211 by either physically moving the array 211 or changing the beam location by controlling the parameters of the imaging apparatus 202 in a conventional manner.

In an even more manual approach, the operator in step 300 observes a full ultrasound scanned image initially obtained, and visually identifies the characteristic feature of interest. Such feature will occur at one or more lines of the scanned image, and represents the response of the stent 32 within the image. The operator identifies the respective line or lines of the scanned image and enters such information into the analyzer module 204. The data from those respective lines is then analyzed in step 304.

Figure 19:
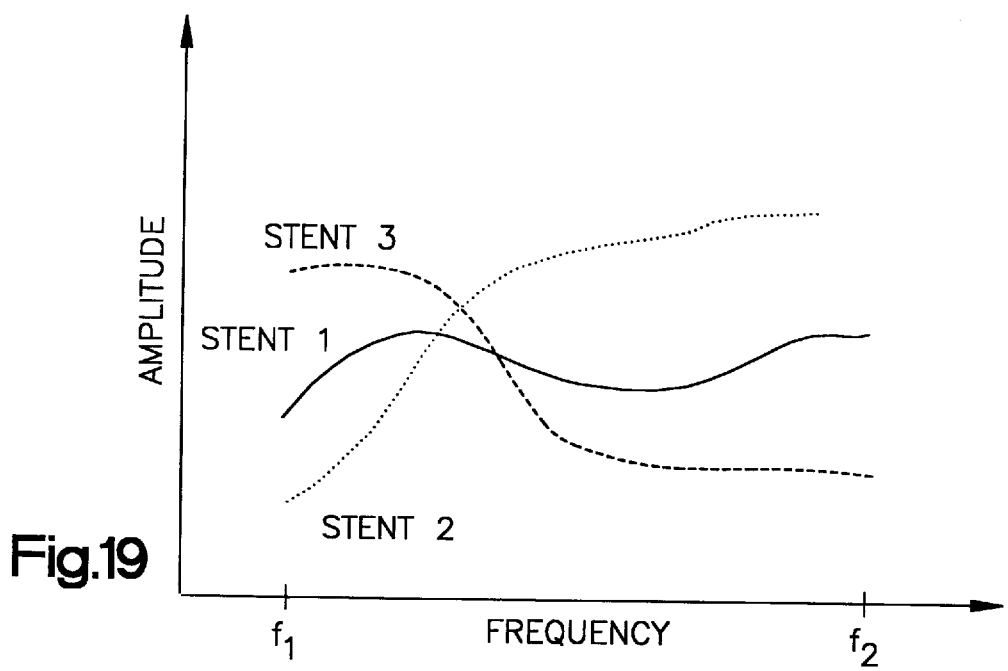
FIG. 19 is a graph illustrating signatures for three different stents in accordance with the present invention.

FIG. 19 represents the manner in which different stents and/or types of stents can exhibit different signatures with respect to frequency response over a predefined band or another predefined parameter, for example. As is shown in FIG. 19, stents 1 thru 3 may exhibit different amplitudes of reflected/reradiated energy across a frequency band f1 to f2. This information is stored in the signature database 242 based on empirical measurements, modeling, etc., for example.

Figure 20:
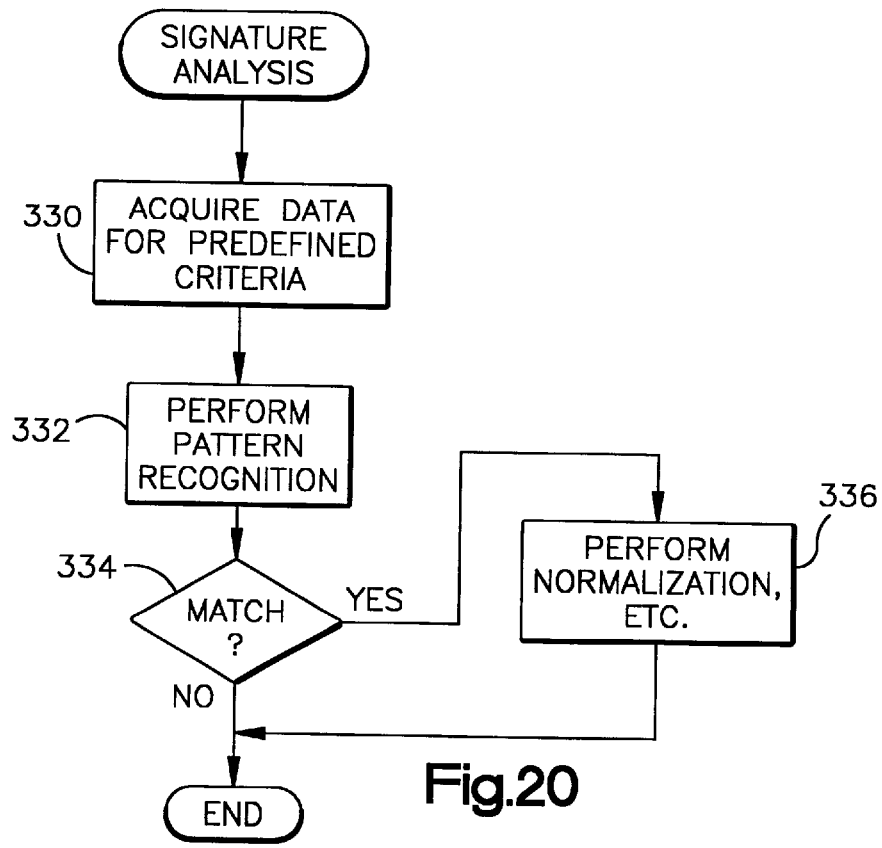
FIG. 20 is a flowchart suitable for programming the system to perform pattern recognition in accordance with the present invention.

FIG. 20 illustrates a process by which the analyzer module 204 is programmed to utilize signature recognition as part of the analysis step 304 in FIG. 16. For example, the analyzer module 204 in step 330 acquires from the data storage memory 234 data meeting a predefined criteria. Such data may be frequency response data across the frequency band f1 to f2 similar to that shown in FIG. 19. Next, in step 332 the DSP 236 is employed to attempt to match the data obtained in step 330 with one of the patterns stored in the signature database 242 using known matching techniques. In step 334, the analyzer module 204 determines if the acquired data matches within a predetermined degree one of the patterns stored in the signature database 242. If yes, it is concluded that information pertaining to the stent 32 under study is available. Such information may be prestored together with the signature data in the database 242. In step 336, the analyzer 204 utilizes such information to facilitate the diagnosis. For example, such information may be helpful in normalizing the acquired data or choosing the particular evaluation criteria to be applied to the data obtained from the stent 32. Also, by being able to differentiate between different stents non-invasively, the present invention is particularly useful with respect to patients for whom there are no records of the particular stent which has been implanted. If in step 334 the analyzer module 204 is unable to match the acquired data to a signature stored in the database 242, the analyzer module may be programmed to proceed with a standard default analysis, for example.

It will therefore be appreciated that the present invention provides a means for early detection of restenosis within a stent. By detecting restenosis early, a patient can be placed on preventative drug therapy, an exercise regimen, etc., and possibly avoid surgery in the future. Moreover, the present invention allows such procedures to be carried out using predominantly existing equipment so as to help minimize costs associated with healthcare.

The present invention is not limited only to the aspect of non-invasive early detection of restenosis in stents, but also may include the additional steps of treating the restenosis. Since the invention provides for early detection, non-invasive and/or less invasive methods of treatment may be employed. For example, the present invention includes the additional steps such as radiation treatment, photodynamic therapy via a catheter, mechanical removal of the restenosis via catheter, etc. Furthermore, drug based treatments such as subcutaneous angiopectin treatment may be employed based on early detection in accordance with the present invention. The stent site is perfused with the drug to prevent/slow the restenosis process. See, e.g., M. K. Hong et al., "Continuous Subcutaneous Angiopectin Treatment Significantly Reduces Neointimal Hyperplasia in a Porcine Coronary In-Stent Restenosis Model", Circulation, 95:2, 1997.

Although the invention has been shown and described with respect to certain preferred embodiments, it is obvious that equivalents and modifications will occur to others skilled in the art upon the reading and understanding of the specification. For example, while the present invention has been described primarily in the context of an implant device which is a stent, other type devices can also be used. In addition, while particular existing ultrasonic imaging apparatuses are mentioned, the present invention has utility with other existing and future ultrasonic apparatuses. For example, the present invention also contemplates the use of future ultrasonic techniques such as nondiffracting X waves presently being discussed in the literature. Moreover, a technique such as modulation of an ultrasonic carrier signal at or near the resonances of the implant device can be utilized to improve signal-to-noise ratios. Also, time-reversal techniques may be employed to the ultrasonic signals transmitted into and received from the body to minimize the effects of noise, energy losses, etc. The present invention includes all such equivalents and modifications, and is limited only by the scope of the following claims.

What is claimed is:

1. An analyzer apparatus for analyzing restenosis associated with a stent implanted within a living body, comprising:
   an input for receiving ultrasonic data from an ultrasonic imaging apparatus;
   digital memory for storing the ultrasonic data at least temporarily;
   a processor for analyzing the ultrasonic data, the processor being configured to analyze the data in accordance with at least one predefined criteria to diagnose a degree of restenosis experienced by the stent; and
   an output for outputting information indicative of the diagnosis.

2. The apparatus of claim 1, wherein the processor analyzes the data based on predefined knowledge of a mechanical transfer function of the stent stored in the digital memory.

3. The apparatus of claim 1, wherein the processor analyzes the data by detecting a change in amplitude of the ultrasonic data relative to a predefined criteria.

4. The apparatus of claim 1, wherein the processor analyzes the data by detecting a reduction in resonance of the stent relative to a predefined criteria.

5. The apparatus of claim 1, wherein the processor analyzes the data by detecting a change in transfer function relative to a predefined criteria.

6. The apparatus of claim 1, wherein the processor analyzes the data by calculating an amplitude decay rate.

7. The apparatus of claim 1, further comprising a signature database for prestoring signature data associated with a plurality of different stents.

8. The apparatus of claim 7, wherein the processor analyzes the data based on the signature data stored in the signature database.

9. The apparatus of claim 8, wherein the processor performs pattern matching between the data and the signature data.

10. The apparatus of claim 9, wherein the processor comprises a digital signal processor.

11. The apparatus of claim 1, wherein the input is configured to receive ultrasonic data from an RF output of an ultrasonic imaging apparatus.

12. The apparatus of claim 11, further comprising an interface for providing remote control commands to the ultrasonic imaging apparatus.

13. The apparatus of claim 12, wherein the processor is configured to provide control commands to adjust a position of an ultrasonic beam produced by the ultrasonic imaging apparatus.

14. The apparatus of claim 13, wherein the control commands are provided in accordance with a predefined criteria to irradiate the stent with the ultrasonic beam.

15. A system for analyzing restenosis associated with a stent implanted within a living body, comprising:

- an ultrasonic apparatus for non-invasively providing ultrasonic data related to the stent;
- digital memory for storing the ultrasonic data at least temporarily;
- a processor for analyzing the ultrasonic data, the processor being configured to analyze the data in accordance with at least one predefined criteria to diagnose a degree of restenosis experienced by the stent; and
- an output for outputting information indicative of the diagnosis.

16. The system of claim 15, wherein the processor analyzes the data based on predefined knowledge of a mechanical transfer function of the stent stored in the digital memory.

17. The system of claim 15, wherein the processor analyzes the data by detecting a change in amplitude of the ultrasonic data relative to a predefined criteria.

18. The system of claim 15, wherein the processor analyzes the data by detecting a reduction in resonance of the stent relative to a predefined criteria.

19. The system of claim 15, wherein the processor analyzes the data by detecting a change in content relative to a predefined criteria.

20. The system of claim 15, wherein the processor analyzes the data by calculating an amplitude decay rate.

21. The system of claim 15, further comprising a signature database for prestoring signature data associated with a plurality of different stents.

22. The system of claim 21, wherein the processor analyzes the data based on the signature data stored in the signature database.

23. The system of claim 22, wherein the processor performs pattern matching between the data and the signature data.

24. The system of claim 23, wherein the processor comprises a digital signal processor.

25. A computer program for analyzing restenosis associated with a stent implanted within a living body, the computer program being stored on a machine-readable medium and comprising instructions and data for carrying out the following steps:

- analyzing ultrasonic data obtained from the stent in accordance with at least one predefined criteria; and
- diagnosing a degree of restenosis experienced by the stent based on the analysis of the ultrasonic data.

* * * * *